United States Patent [19]

Shishido et al.

[11] 4,200,464
[45] Apr. 29, 1980

[54] SILVER HALIDE COLOR PHOTOGRAPHIC MATERIALS CONTAINING A UV FILTER COMPOUND

[75] Inventors: Tadao Shishido; Naoki Arai, both of Minami-ashigara, Japan

[73] Assignee: Fuji Photo Film Co., Ltd., Minami-ashigara, Japan

[21] Appl. No.: 876,801

[22] Filed: Feb. 10, 1978

Related U.S. Application Data

[63] Continuation of Ser. No. 732,830, Oct. 15, 1976, abandoned.

[30] Foreign Application Priority Data

Oct. 16, 1975 [JP] Japan .................................. 50-124751

[51] Int. Cl.² ............................................... G03C 1/84
[52] U.S. Cl. ...................................... 430/512; 430/510
[58] Field of Search ..................... 96/56, 84 R, 84 U; 260/340.5 R

[56] References Cited

U.S. PATENT DOCUMENTS

| | | | |
|---|---|---|---|
| 2,433,491 | 12/1947 | Synerholm et al. | 260/340.5 R |
| 3,052,636 | 9/1962 | Strobel et al. | 252/300 |
| 3,278,448 | 10/1966 | Laverer et al. | 96/84 UV |
| 3,705,805 | 12/1972 | Nittel et al. | 96/84 R |
| 3,707,375 | 12/1972 | Reiichi et al. | 96/84 UV |
| 3,787,409 | 1/1974 | Grunberg et al. | 260/347.5 R |
| 3,910,959 | 10/1975 | Valcet | 260/340.5 R |

Primary Examiner—Jack P. Brammer
Attorney, Agent, or Firm—Sughrue, Rothwell, Mion, Zinn and Macpeak

[57] ABSTRACT

Silver halide color photographic sensitive materials which contain at least one compound represented by the following formulae (I) or (II):

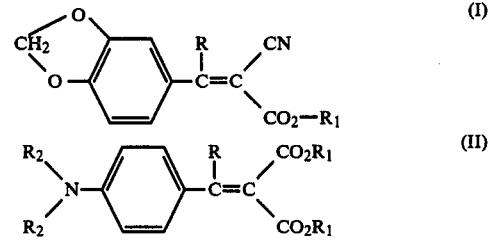

wherein R represents a hydrogen atom or a lower alkyl group having 1 to 5 carbon atoms and $R_1$ and $R_2$ each represents an alkyl group having 1 to 20 carbon atoms, wherein $R_1$ and $R_2$ may be the same as or different from each other, and the sum total of carbon atoms of $R_1$ and $R_2$ is 5 or more.

8 Claims, No Drawings

SILVER HALIDE COLOR PHOTOGRAPHIC MATERIALS CONTAINING A UV FILTER COMPOUND

This is a continuation, of application Ser. No. 732,830, filed Oct. 15, 1976 now abandoned.

BACKGROUND OF THE INVENTION

1. Field of the Invention

The present invention relates to silver halide color photographic sensitive materials, particularly, to silver halide color photographic materials having improved color reproduction which are not affected by differences in ultraviolet absorption characteristics of a camera lens. Further, the present invention relates to a method of improving variations in color balance caused by differences in the ultraviolet ray absorption of a camera lens.

2. Description of the Prior Art

In available cameras, lenses which are coated with an ultraviolet ray absorbing agent or lenses which are not coated with an ultraviolet ray absorbing agent are in use.

When an object is photographed using these two kinds of lenses under the same conditions and the silver halide photographic sensitive materials thus exposed are processed under the same conditions, the resulting photographic images generally have different color tones. This phenomenon results from the fact that the percent transmission of ultraviolet rays of the lens and the wavelength range of light absorbed by the lens vary depending on the presence or absence of an ultraviolet ray absorbing agent.

Hitherto, many compounds have been known as ultraviolet ray absorbing agents. However, there are only a few compounds which satisfy the following three characteristics:

1. They effectively absorb ultraviolet rays of 300 to 400 m$\mu$ and do not absorb visible rays of above 420 m$\mu$;
2. They do not change in color upon development;
3. They do not have a harmful influence upon photographic sensitive materials at preparation, during storage or at development thereof.

Many available ultraviolet ray absorbing agents run out or discolor during the development processing and some of them have a harmful influence on photographic sensitive emulsions. Compounds analogous to the compounds of the present invention are described in U.S. Pat. No. 3,278,448. However, they have insufficient absorption in the wavelength range of 300 to 400 nm, and, consequently, they do not satisfy the above described absorption characteristics or emulsification or dispersion thereof is unsatisfactorily carried out.

SUMMARY OF THE INVENTION

We have performed many studies in order to develop photographic ultraviolet ray absorbing agents which can be dispersed in a finely divided emulsified state into a hydrophilic colloid solution (for example, a gelatin sol) in the presence or absence of a small amount of a water-insoluble organic solvent having a high boiling point and which have properties such that an emulsified dispersion thereof is stable and they do not cause the photographic hydrophilic colloid layers to become opaque or hardly soften the layers in addition to having the above described three characteristics. As a result of such studies, we found that the compounds represented by formulae (I) and (II) below are particularly suitable to meet the objects of this invention.

Accordingly, an object of the present invention is to provide silver halide color photographic sensitive materials having improved color reproduction which is not affected by differences in the ultraviolet ray absorption characteristics of a camera lens.

Another object of the present invention is to provide silver halide photographic sensitive materials showing less variations in color balance with various camera lenses and whose photographic properties such as sensitivity, fog, etc., are not adversely affected.

A further object of the present invention is to provide a method of reducing variations in the color balance of silver halide color photographic sensitive materials.

These objects of the present invention have been attained by adding at least one compound represented by the following formulae (I) and (II) to silver halide color photographic sensitive materials.

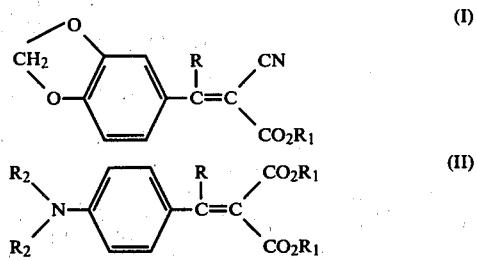

In these formulae, R represents a hydrogen atom or an alkyl group having 1 to 5 carbon atoms and $R_1$ and $R_2$ each represents an alkyl group having 1 to 20 carbon atoms. $R_1$ and $R_2$ may be the same or different from one another, and the sum total of carbon atoms thereof is 5 or more. In formulae (I) and (II), it is preferred that R represent a hydrogen atom, $R_1$ represent a branched or straight chain alkyl group having 8 to 16 carbon atoms, and $R_2$ represent a lower alkyl group (e.g., having up to 4 carbon atoms).

DETAILED DESCRIPTION OF THE INVENTION

Typical examples of compounds represented by formulae (I) and (II) of the present invention are described in the following. (The absorption maximum wavelength thereof was measured under the condition of $5\times10^{-5}$ mol/l in methanol at room temperature (about 20°–30° C.).)

Compound 1

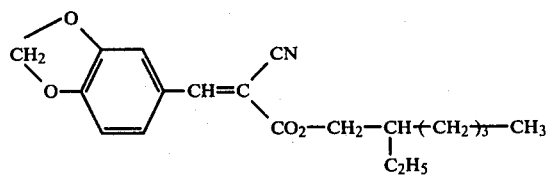

2-Ethylhexyl-3,4-methylenedioxy-$\alpha$-cyanocinnamate
Melting point: 58°–59° C. $\lambda_{max}^{MeOH}$ 363 m$\mu$ Compound 2

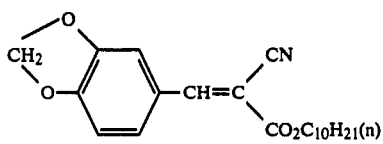

n-Decyl-3,4-methylenedioxy-α-cyanocinnamate
Melting point: 62°–63° C. $\lambda_{max}^{MeOH}$ 363 mμ

Compound 3

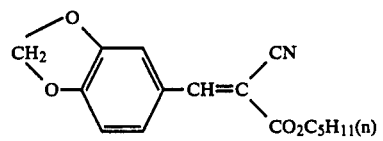

n-Pentyl-3,4-methylenedioxy-α-cyanocinnamate
Melting point: 71° C. $\lambda_{max}^{MeOH}$ 363 mμ

Compound 4

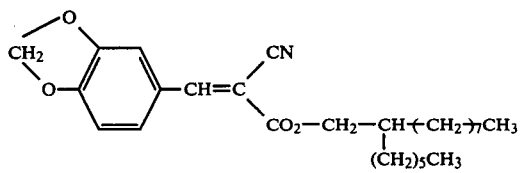

2-Hexyldecyl-3,4-methylenedioxy-α-cyanocinnamate
Oil $\lambda_{max}^{MeOH}$ 363 mμ

Compound 5

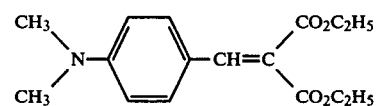

Ethyl p-dimethylamino-α-ethoxycarbonylcinnamate
Melting point: 108°–109° C. $\lambda_{max}^{MeOH}$ 378 mμ

Compound 6

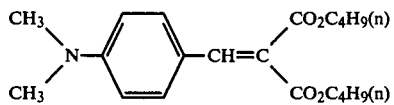

n-Butyl p-dimethylamino-α-n-butoxycarbonylcinnamate
Melting point: 61° C. $\lambda_{max}^{MeOH}$ 378 mμ

Compound 7

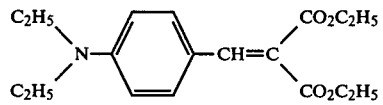

Ethyl p-diethylamino-α-ethoxycarbonylcinnamate
Oil $\lambda_{max}^{MeOH}$ 379 mμ

Compound 8

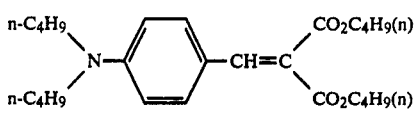

n-Butyl p-di-n-butylamino-α-n-butoxycarbonylcinnamate
Oil $\lambda_{max}^{MeOH}$ 379 mμ

These compounds can be synthesized from the corresponding cyanoacetic acid esters or malonic acid esters and substituted benzaldehydes or ketones by known methods (refer to, for example, Beilsteins, *Handbuch der Organischen Chemie* (fourth edition), Vol. 10, page 521 (1942)). The synthesis of typical compounds is described below.

Synthesis 1 (Synthesis of Compound 1)

51 g of piperonal, 40 g of 2-ethylhexyl cyanoacetate, 4 g of ammonium acetate and 12 ml of glacial acetic acid were mixed. The mixture was stirred with heating at 120° to 130° C. on an oil bath for 2 hours. After cooling to room temperature, the resultant crystals were recrystallized from 130 ml of methanol. 38 g of needle-like crystals of Compound 1 having a 58° to 59° C. melting point were obtained.

Synthesis 2 (Synthesis of Compound 8)

179 g of p-dimethylaminobenzaldehyde, 260 g of di-n-butyl malonate, 2.4 g of benzoic acid, and 6 ml of piperidine were added to 600 ml of benzene. The mixture was refluxed with heating for 3.5 hours on a water bath. Solvent was then removed by distillation at reduced pressure. The crystals obtained by cooling were recrystallized from petroleum ether. 236 g of needle-like crystals of Compound 8 having a 61° C. melting point were obtained.

It is preferred that the compounds of the present invention not substantially absorb visible rays of above 420 nm and have an absorption maximum at 350 to 390 nm, particularly preferably at 360 to 380 nm.

The compounds of the present invention are substantially insoluble in water and have a high solubility in water insoluble organic solvents having a high boiling point, though they are oily at room temperature.

The compounds of the present invention can be added to photographic hydrophilic colloid layers by dissolving them in a water insoluble organic solvent having a high boiling point (preferably 120° C. or more) and emulsifying or by dispersing them directly in the emulsion (for example, see U.S. Pat. Nos. 2,739,888 and 3,352,681 for useful procedures).

The compounds of the present invention are incorporated in photographic elements of a color sensitive materials. For example, they may be added to a protective layer, a back layer, a light-sensitive silver halide emulsion layer, a yellow filter layer, an intermediate layer or a subbing layer. However, it is more preferred to add them to a surface protective layer (preferably, a gelatin protective layer) or a blue-sensitive silver halide emulsion layer (preferably, a gelatin layer having silver halide grains dispersed therein).

The amount of the compounds of the present invention in the layer is above about $5 \times 10^{-4}$ g/m$^2$, particularly 0.05 g/m². The upper limit is not limited and depends on factors such as cost and layer quality desired.

Examples of the water insoluble organic solvents having a high boiling point used for dispersing the compounds of the present invention include alkyl esters of phthalic acid (for example, dibutyl phthalate or dioctyl phthalate, etc.), trimellitic acid esters (for example, tri-t-octyl trimellitate), aromatic esters, phosphoric acid esters (for example, diphenyl phosphate, triphenyl phosphate, tricresyl phosphate or dioctylbutyl phosphate), citric acid esters (for example, tributyl acetylcitrate) and alkylamides (for example, N,N-diethyl laurylamide), etc.

As hydrophilic colloid materials used for the photographic elements and particularly for the hydrophilic colloid layers in the silver halide photographic sensitive materials, there are used many known materials such as gelatin, gelatin derivatives, such as the reaction product of gelatin with acid halides, acid anhydrides, isocyanates, bromoacetic acid, alkanesultones, vinylsulfonamides, maleinimides, polyalkyleneoxides or epoxy compounds as described in U.S. Pat. Nos. 2,614,928, 3,132,945, 3,186,846, 3,312,553, British Pat. Nos. 861,414, 1,033,189, 1,005,784, Japanese Patent Publication No. 26845/67, with examples including phthalated gelatin, succinated gelatin, maleated gelatin, etc., carboxycellulose derivatives, such as carboxymethyl cellulose, cellulose sulfate esters, polyacrylamides, polyvinyl alcohols and polyvinyl pyrrolidones, etc.

The compounds of the present invention may be used together with known photographic antioxidants (for example, hydroquinone derivatives (e.g., as described in British Pat. Nos. 558,258, 557,750, 557,802, 752,146, 1,086,208, etc., U.S. Pat. Nos. 3,700,453, 2,701,197, 2,899,334, 2,728,659, 2,336,327, 2,732,300, 2,403,721, 3,243,294, 3,816,126, 3,582,333, etc., *Chemical Abstracts*, 58, 6367h, West German Patent Application (OLS) Nos. 2,149,789, 2,505,016, etc., Japanese Patent Application (OPI) Nos. 156438/1975, 106329/1974, etc., Japanese Patent Publication No. 21249/1975, etc.), catechol derivatives, aminophenol derivatives and gallic acid derivatives, etc.) or known photographic ultraviolet ray absorbing agents such as benzotriazole type compounds or benzophenone type compounds under conditions which satisfy the above described objects of the present invention.

The silver halide color sensitive materials of the present invention contain a support, a silver halide emulsion layer, a protective layer and an intermediate layer, and optionally a filter layer, a subbing layer and a back layer, etc.

As a support, there may be used, for example, films of polyethylene terephthalate, polycarbonate, polystyrene, polypropylene or cellulose acetate, etc., polyethylene laminated paper or baryta paper.

As the silver halide for the silver halide emulsion, there may be used silver bromide, silver chloride, silver iodobromide, silver bromochloride or silver iodobromochloride, etc. The silver halide emulsions can be produced by any known process.

The silver halide emulsions may be sensitized by chemical sensitizing agents (for example, sulfur sensitizing agents such as thiourea, allylthiocarbamide, allylisothiocyanate or cystine, etc., gold compounds such as potassium chloroaurate, auric trichloride or potassium auric thiocyanate, etc., and other noble metal sensitizing agents) and known reduction sensitizing agents, etc., if desired.

Further, known stabilizing agents or anti-fogging agents such as triazoles, imidazoles or azaindenes may be added to the silver halide emulsions, if desired.

Moreover, various color image forming agents can be used for the color photographic sensitive materials of the present invention. Examples thereof include benzoylacetoanilide type and pivaloylacetoanilide type 2-equivalent or 4-equivalent yellow couplers (e.g., as described in U.S. Pat. Nos. 2,875,057, 3,265,506, 3,408,194, 3,551,155, 3,582,322, 3,725,072, 3,891,445, etc., West German Patent No. 1,547,868, etc., West German Patent Application (OLS) Nos. 2,213,461, 2,219,917, 2,261,361, 2,263,875, 2,414,006, etc.), pyrazolone type, indazolone type or cyanoacetyl type 2-equivalent or 4-equivalent magenta couplers (e.g., as described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908, 3,891,445, etc., West German Patent No. 1,810,464, etc., West German Patent Application (OLS) Nos. 2,408,665, 2,417,945, 2,418,959, 2,424,467, etc., Japanese Patent Publication No. 6031/1965, etc.), phenol type or naphthol type 2-equivalent or 4-equivalent cyan couplers (e.g., as described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411, etc., West German Patent Application (OLS) Nos. 2,414,830, 2,454,329, etc., Japanese Patent Application (OPI) No. 59838/1973, etc.) and cyan or magenta colored couplers (the above described 2-equivalent yellow, magenta or cyan couplers may be DIR couplers, if desired (e.g., as disclosed in U.S. Pat. Nos. 3,227,554, 3,617,291, 3,701,783, 3,790,384, 3,632,345, etc., West German Patent Application (OLS) Nos. 2,414,006, 2,454,301, 2,454,329, etc., British Pat. No. 953,454, etc., Japanese Patent Application No. 146570/1975, etc.)). It is preferred that these couplers be non-diffusible. Further, redox compounds which release a diffusible dye (e.g., as described in U.S. Pat. Nos. 3,928,312, U.S.B. 351,673 (U.S. patent application Ser. No. 351,673, filed on Apr. 16, 1973), etc., West German Patent Application (OLS) Nos. 2,406,653, 2,406,626, etc.) or couplers which release a diffusible dye (e.g., as described in U.S. Defensive Publication No. T-900029, U.S. Pat. No. 3,227,550, etc., Canadian Pat. Nos. 928,559, 928,560, etc.) or dye developers (e.g., as described in U.S. Pat. Nos. 2,983,606, 3,233,601, 3,019,107, 3,320,062, 3,345,163, 3,086,005, etc., Japanese Patent Publication Nos. 182/1959, 4380/1959, 5189/1959, 12432/1960, 444/1963, 4378/1960, 11377/1960, 12393/1961, 2241/1962, 2244/1962, 8781/1962, 182/1960, 18332/1960, 32130/1973, 43950/1971, 2618/1974, etc.) may be used.

In addition, known additives (for example, spectral sensitizing agents, color stain preventing agents, color fading preventing agents, hardening agents, surface active agents or antistatic agents, etc.) may be added, if desired.

Examples of layer structures of the silver halide color photosensitive materials of the present invention are as follows:

(1) A multilayer color sensitive material which is prepared by applying to a support, in this order, an antihalation layer, a gelatin intermediate layer, a red-sensitive emulsion layer (which may be composed of a single layer or may have a multilayer structure consisting of a sensitive silver halide layer having a comparatively low sensitivity and a silver halide emulsion layer having a higher sensitivity thereon, or a multilayer structure consisting of three or more of such layers), a gelatin intermediate layer, a green-sensitive emulsion layer (which may be composed of a single layer or may have a multilayer structure as described for the red-sensitive emulsion layer), a yellow filter layer, a blue-sensitive emulsion layer (which may be composed of a single layer or may have a multilayer structure) and a protective layer, which is suitable as a high speed color negative film;

(2) A multilayer color sensitive material which is prepared by applying to a support, in this order, an antihalation layer, a gelatin intermediate layer, red-sensitive emulsion layers (a red-sensitive emulsion layer having a higher sensitivity and a red-sensitive emulsion layer having a comparatively low sensitivity thereon), a gelatin intermediate layer, a green-sensitive layer having a high sensitivity, a yellow filter layer, a blue-sensitive emulsion layer, a green-sensitive emulsion layer having a comparatively low sensitivity and a protective layer, which is suitable as a high speed color reversal film;

(3) A multilayer color sensitive material which is prepared by applying to a support, in the order, an antihalation layer, a gelatin intermediate layer, a blue-sensitive emulsion layer, a gelatin intermediate layer, a red-sensitive emulsion layer, a gelatin intermediate layer, a green-sensitive emulsion layer, a yellow filter layer and a protective layer, which is suitable as an 8 mm color film.

In a color sensitive material having layer structure (1), the compound of the present invention is preferably added to at least one of the protective layer, the blue-sensitive emulsion layer having a higher sensitivity or the blue-sensitive emulsion layer having a comparatively low sensitivity.

In a color sensitive material having layer structure (2), the compound of the present invention is preferably added to at least one of the protective layer, the green-sensitive emulsion layer having a comparatively low sensitivity or the blue-sensitive emulsion layer, and, particularly, at least one of the protective layer and the green-sensitive emulsion layer having a comparatively low sensitivity.

In color sensitive materials having layer sturcture (3), though the compound of the present invention may be added to any layer, it is more preferred to add it to at least one of the protective layer, the yellow filter layer or the green-sensitive emulsion layer. Examples of layer structures of the types (1) and (2) described above are disclosed in British Pat. No. 923,045, U.S. Pat. No. 3,843,369, West German Patent Application (OLS) Nos. 2,453,664, 2,453,654, etc.

As the silver halide color photographic sensitive materials of the present invention, there are color negative films, color reversal films, color direct positive films and diffusion transfer color sensitive materials, etc.

It goes without saying that the compounds of the present invention can be used for sensitive materials having layer structures other than the above described ones.

The silver halide sensitive materials of the present invention can be processed by any conventional development processing or by a DIR color processing solution included in the sensitive material. For example, the process described in *Journal of the Society of Motion Picture and Television Engineers*, Volume 61, (1953), pages 667 to 701, can be used.

With the silver halide color sensitive materials of the present invention, there are no variations in the color reproduction due to differences in the ultraviolet ray absorption of the camera lens used. Further, photographic properties such as sensitivity or fogging are not harmfully affected and there is no static fog which is formed during production or storage of the sensitive materials.

The present invention will now be illustrated in greater detail by several Examples. Unless otherwise indicated, all parts, percents, ratios and the like are by weight.

EXAMPLE 1

As illustrated in Table 1 below, to a mixture consisting of 1,000 g of a 10% aqueous solution of gelatin and 75 ml of a 5% aqueous solution of sodium dodecylbenzene sulfonate, 40 ml of dibutyl phthalate, 100 ml of ethyl acetate and 20 ml of a 20% solution of sorbitan monolaurate in methanol were added and dispersed using a colloid mill for 5 minutes to produce Emulsified Dispersion A, which was used as a control.

120 g of Compound 1 was dispersed in an identical sample of Emulsified Dispersion A in the same manner as described above to produce Emulsified Dispersion B. Similarly, Emulsified Dispersion C containing 120 g of Compound 4, Emulsified Dispersion D containing 120 g of Compound 6, Emulsified Dispersion E containing 100 g of Compound 6 and 20 g of 2-(2-hydroxy-5-t-butyl)-phenylbenzotriazole and Emulsified Dispersion F containing 120 g of n-decyl 4-methoxy-α-cyanocinnamate were prepared.

TABLE 1

| Emulsified Dispersion | A | B | C | D | E | F |
|---|---|---|---|---|---|---|
| 10% Aqueous solution of gelatin | 1,000 g | 1,000 g | 1,000 g | 1,000 g | 1,000 g | 1,000 g |
| 5% Aqueous solution of sodium dodecylbenzene sulfonate | 75 ml | 75 ml | 75 ml | 75 ml | 75 ml | 75 ml |
| Dibutyl phthalate | 40 ml | 40 ml | 40 ml | 40 ml | 40 ml | 40 ml |
| Ethyl acetate | 100 ml | 100 ml | 100 ml | 100 ml | 100 ml | 100 ml |
| 20% Solution of sorbitan monolaurate in methanol | 20 ml | 20 ml | 20 ml | 20 ml | 20 ml | 20 ml |
| Compound 1 | — | 120 g | — | — | — | — |
| Compound 4 | — | — | 120 g | — | — | — |
| Compound 6 | — | — | — | 120 g | 100 g | — |
| 2-(2-Hydroxy-5-t-butyl)-phenylbenzotriazole | — | — | — | — | 20 g | — |
| n-Decyl 4-Methoxy-α-cyanocinnamate | — | — | — | — | — | 120 g |

The following layers were then applied to a support.

First Layer

An antihalation layer containing the following dyes mordanted with a mordant:

| | coating amount |
|---|---|
| Cyan Dye | |
| NaO₃SH₂CNH O OH<br>    \|\|<br>NaO₃S  SO₃Na<br>   OH O NHCH₂SO₃Na<br>(anthraquinone structure) | about 200 mg/m² |
| Magenta Dye<br>KOOC—C——C=(CH)₃—C——C—COOK<br>     \|\|         \|   \|      \|\|<br>     N  C=O  C  N<br>      \\N/    HO    \\N/<br>       \|             \|<br>     (C₆H₄-SO₃K)  (C₆H₄-SO₃K) | " |
| Yellow Dye<br>NaOOC——CH—N=N—⟨C₆H₄⟩—SO₃Na<br>     \|\|  \|<br>     N  C=O<br>      \\N/<br>       \|<br>     (C₆H₄-SO₃Na) | " |
| Mordant<br>⟨CH₂—CH⟩ₓ⟨CH₂—CH⟩ᵧ<br>              \|<br>              C=O<br>              \|<br>              CH₃<br>              NH<br>              \|<br>   C=N—NHC<br>   \|       \\<br>   CH₃      NH₂ · CH₃COOH<br>x/y = 77/23 | 0.5 g/g of binder |

Second Layer

A red-sensitive silver iodobromide(I: 4 mol%)-gelatin emulsion layer containing oil-soluble non-diffusing cyan couplers* (molar ratio of silver/coupler: 25, amount of silver coated: 30 mg/100 cm²).

Third Layer

An intermediate layer containing gelatin.

Fourth Layer

A green-sensitive silver iodobromide(I: 3.5 mol%)-gelatin emulsion layer containing non-diffusing magenta couplers** (molar ratio of silver/coupler: 35, amount of silver coated: 20 mg/100 cm²).

Fifth Layer

A gelatin layer having a yellow filter function by using the same yellow dye (300 mg/m²) as described for the antihalation layer.

Sixth Layer

A silver iodobromide(I: 3 mol%)-gelatin emulsion layer containing a non-diffusing yellow coupler*** (molar ratio of silver/coupler: 10, amount of silver coated: 15 mg/100 cm²).

Seventh Layer

A layer of the above described Emulsified Dispersion A applied in an amount of 1.93 g/m² (dry basis; thickness of the layer: 1.8μ), which was called Sample 1.

Similarly, Sample 2, Sample 3, Sample 4, Sample 5 and Sample 6 were produced using Emulsified Dispersion B, Emulsified Dispersion C, Emulsified Dispersion D, Emulsified Dispersion E and Emulsified Dispersion F instead of Emulsified Dispersion A.

In order to measure variations in the color balance of the photographic sensitive materials caused by use of different kinds of camera lens wherein the percent transmission of ultraviolet rays differed from lens to lens, a gray chart was photographed using a camera equipped with a lens of a high percent transmission of ultraviolet rays and a camera equipped with the same lens as described above but having a filter which cut rays of wavelengths of below 390 mμ. The resultant negative images in both cases were then measured and the red light density measured, the green light density measured and the blue light density measured in both cases and compared with each other. The differences of the densities measured under each light were shown in Table 2.

It can be understood from Table 2 that variations in blue density were less in the photographic sensitive materials using Compounds 1, 4 and 6, that the photographic sensitive materials are less affected by variations in the percent transmission of ultraviolet rays and that gray balance was excellent.

TABLE 2

| Density[1] Difference | Sample | | | | | |
|---|---|---|---|---|---|---|
| | (1) | (2) | (3) | (4) | (5) | (6) |
| Red | 0 | 0 | 0 | 0 | 0 | 0 |
| Green | 0 | 0 | 0 | 0 | 0 | 0 |
| Blue | 0.14 | 0.08 | 0.09 | 0.08 | 0.09 | 0.12 |

[1]The values in Table 2 represent the difference between the image density in the case of photographing using a lens through which ultraviolet rays completely pass and the image density in the case of photographing using the same lens equipped with a filter which cut rays below 390 mμ (red, green or blue light density, as indicated).

The above described couplers have the following chemical formulae:

* Cyan Couplers

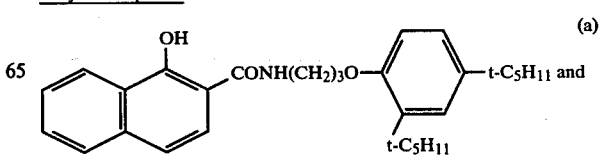

(a)

-continued

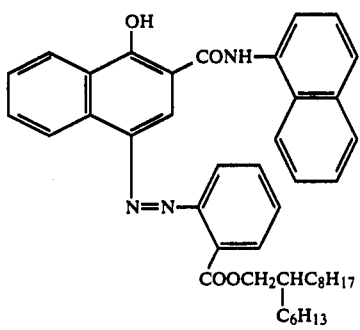

(a weight ratio a : b of 5 : 1)

| | | |
|---|---|---|
| (b) | Sodium bromide | 1.5 g |
| | Hydroxylamine sulfate | 2.5 g |
| | EDTA | 2.5 g |
| | 4-[N-ethyl-N-(β-ethoxyethyl)amino]-2-methylaniline sulfate | 4.7 g |
| | Water to make 1 liter | pH 10.0 |
| | Bleaching solution: | |
| | Water | 600 ml |
| | Ammonium bromide | 150 g |
| | EDTA-Fe(III) sodium salt | 100 g |
| | Glacial acetic acid | 10 ml |
| | EDTA | 10 g |
| | Water to make 1 liter | pH 6.0 |
| | Fixing solution: | |
| | Water | 800 ml |
| | Ammonium thiosulfate (70% aq. soln.) | 140 ml |
| | Sodium bisulfite (anhydrous) | 12 g |
| | Water to make 1 liter | |

** Magenta Couplers

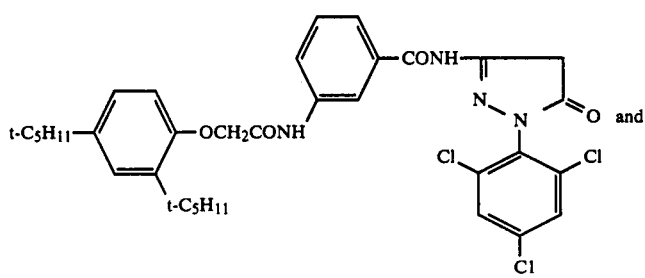
(a)

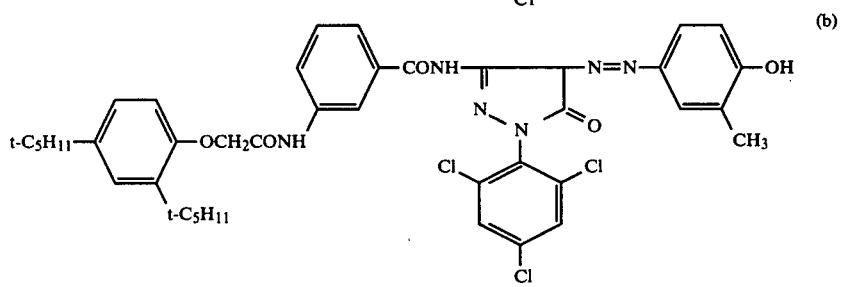
(b)

(a weight ratio a : b of 1 : 1)

*** Yellow Coupler

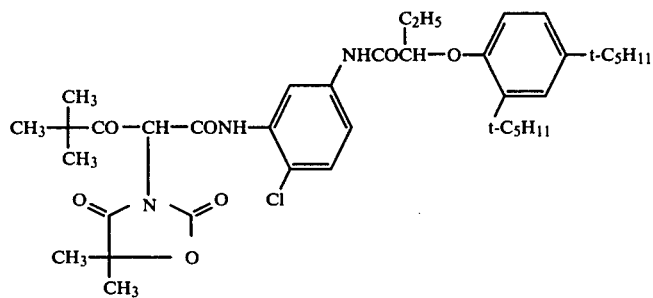

The processing was carried out as follows:

| | Temperature (°C.) | Time |
|---|---|---|
| Color development | 38 | 3 min. and 15 sec. |
| Bleaching | " | 6 min. and 30 sec. |
| Water wash | " | 3 min. and 15 sec. |
| Fixing | " | 6 min. and 30 sec. |
| Water wash | " | 3 min. and 15 sec. |
| Stabilizing | " | 1 min. and 30 sec. |

| Color developing solution: | |
|---|---|
| Water | 800 ml |
| Potassium carbonate (anhydrous) | 38 g |
| Sodium sulfite (anhydrous) | 4 g |

| Stabilizing solution: | |
|---|---|
| Water | 800 ml |
| Formalin (37% aq. soln.) | 5.0 ml |
| Polyethylene glycol | 0.2 g |
| Ethylene glycol | 2 g |
| Water to make 1 liter | |

The same results as those in the Example 1 were also obtained when colloidal silver (about 4 mg/100 cm$^2$) in the antihalation layer and/or colloidal silver (about 1 mg/100 cm$^2$) in the filter layer is employed instead of the dye(s), respectively. Furthermore, the same results as those of the Example 1 were also obtained when a gelatin layer without a yellow filter function was employed instead of the yellow filter layer.

EXAMPLE 2

The 1st layer, the 2nd layer, the 3rd layer, the 4th layer and the 5th layer were provided in the same manner as for the layer structure of Example 1, and the 6th layer was produced as follows using Emulsified Dispersions F, B, C and D in Table 1, respectively. A protective layer of gelatin was coated on the 6th layer. In order to form the 6th layer, Emulsified Dispersion F was incorporated in the amount of 1.93 g/m² in the non-diffusing yellow coupler-containing silver bromoiodide emulsion as described in Example 1 and the blue-sensitive layer was applied in a dry thickness of 5.2μ to produe Sample 7. Emulsified Dispersion F in Sample 7 was replaced with Emulsified Dispersion B to produce Sample 8, with Emulsified Dispersion C to produce Sample 9 and with Emulsified Dispersion D to produce Sample 10. These samples were exposed, processed and measured in the same manner as in Example 1. The results obtained are shown in Table 3.

TABLE 3

| Density | Sample | | | |
|---|---|---|---|---|
| Difference | (7) | (8) | (9) | (10) |
| Red | 0 | 0 | 0 | 0 |
| Green | 0 | 0 | 0 | 0 |
| Blue | 0.13 | 0.10 | 0.10 | 0.09 |

(Density difference in Table 3 has the same meaning as in Example 1.)

It can be understood from Table 3 that the compounds of the present invention have the effect of reducing variations of color balance caused by a differences in camera lens, though added to the blue-sensitive layer.

EXAMPLE 3

Samples 1, 2, 3 and 4 described in Example 1 were examined as follows.

The protective layer of Samples 1, 2, 3 and 4 was rubbed in a dark room by means of a rubber roll having substantially 0 volt of the triboelectric series to cause light emission by discharging. These samples were simultaneously developed in the same manner as in Example 1 and the density of the static marks in each sample was measured. Increased density due to static marks was as shown in Table 4.

TABLE 4

| | Sample | | | |
|---|---|---|---|---|
| Density | (1) | (2) | (3) | (4) |
| Red density | 0 | 0 | 0 | 0 |
| Green density | 0 | 0 | 0 | 0 |
| Blue density | 1.0 | 0.2 | 0.3 | 0.2 |

It is clear from Table 4 that the occurrence of static marks was reduced by the addition of the compounds of the present invention. (Red density, green density and blue density in Table 4 each means image density measured under a red, green or blue light.)

While the invention has been described in detail and with reference to specific embodiments thereof, it will be apparent to one skilled in the art that various changes and modifications can be made therein without departing from the spirit and scope thereof.

What is claimed is:

1. A silver halide color photographic element containing at least one silver halide emulsion layer, said element containing at least one compound represented by the following formula (I) in an amount of at least about 0.05 g/m to function as an ultraviolet ray absorbing material:

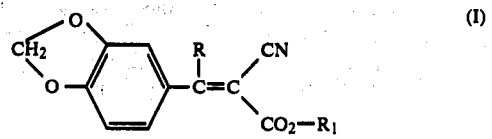

wherein R represents a hydrogen atom or a lower alkyl group having 1 to 5 carbon atoms and $R_1$ represents an alkyl group having 1 to 20 carbon atoms.

2. The silver halide color photographic material of claim 1, wherein R represents a hydrogen and $R_1$ represents a branched or straight chain alkyl group having 8 to 16 carbon atoms.

3. The silver halide color photographic material of claim 1, wherein said compound represented by the formulae (I) is:

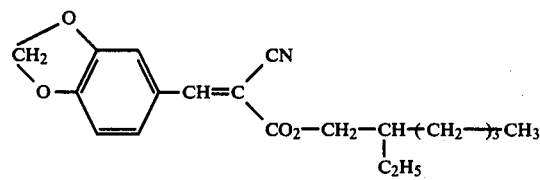

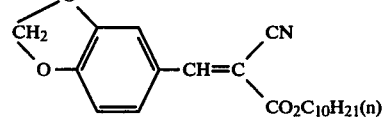

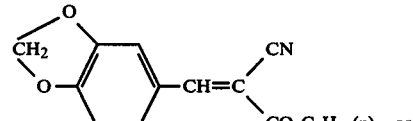

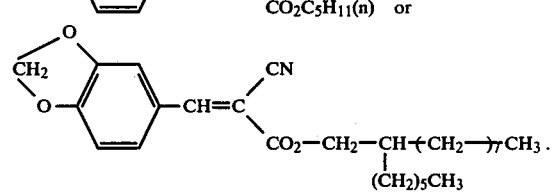

4. The silver halide color photographic material of claim 3, wherein said compound of the formulae (I) is:

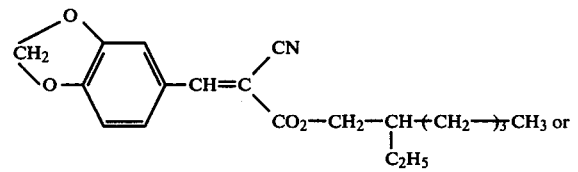

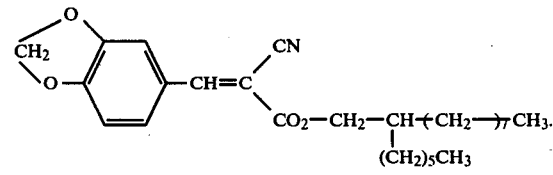

5. The silver halide color photographic material of claim 1, wherein said compound represented by the formulae (I) is present in a surface protective layer of said silver halide color photographic material or a blue-sensitive silver halide emulsion layer of said color photographic material.

6. The silver halide color photographic element of claim 1, wherein R represents a hydrogen atom.

7. The silver halide color photographic material of claim 2, wherein said compound represented by the formula (I) is present in a surface protective layer of said silver halide color photographic material or a blue-sensitive silver halide emulsion layer of said color photographic material.

8. The silver halide color photographic material of claim 6, wherein said compound represented by the formula (I) is present in a surface protective layer of said silver halide color photographic material or a blue-sensitive silver halide emulsion layer of said color photographic material.

* * * * *